United States Patent [19]

Bruns et al.

[11] Patent Number: 5,441,930
[45] Date of Patent: Aug. 15, 1995

[54] ISOMERIC 11-OXATRICYCLO[7.3.02,6]DODECENE DERIVATIVES, THEIR PRODUCTION AND THEIR USE AS FRAGRANCES AND FRAGRANCE COMPOSITIONS CONTAINING THEM

[75] Inventors: Klaus Bruns, Krefeld-Traar; Michael Dischmann, Krefeld; Werner Faber, Willich; Michael Meiertoberens, Krefeld-Fischeln, all of Germany

[73] Assignee: Henkel Kommanditgesellschaft auf Aktien, Duesseldorf, Germany

[21] Appl. No.: 272,437

[22] Filed: Jul. 8, 1994

Related U.S. Application Data

[63] Continuation of Ser. No. 30,233, Mar. 17, 1993, abandoned.

[30] Foreign Application Priority Data

Sep. 17, 1990 [DE] Germany .................. 40 29 424.2

[51] Int. Cl.$^6$ ............................................. A61K 7/46
[52] U.S. Cl. .................................... 512/13; 549/458
[58] Field of Search ......................... 512/13; 549/458

[56] References Cited

U.S. PATENT DOCUMENTS 4,302,363 11/1981 Bruns et al. .................... 252/522 R

FOREIGN PATENT DOCUMENTS 2001243 7/1970 Germany .
2925622 1/1981 Germany .

OTHER PUBLICATIONS

Parfümerie u. Kosmetik, 1986 (67) 714.

*Primary Examiner*—James H. Reamer
*Attorney, Agent, or Firm*—Wayne C. Jaeschke; John E. Drach; Henry E. Millson, Jr.

[57] ABSTRACT

The isomeric 11-oxa-tricyclo[7.3.0.0$^{2,6}$]dodecene derivatives proposed are valuable new odoriferous substances characterized by their different nuances of intense woody notes and extremely high persistence. They can be mixed with each other, or with other odoriferous substances, in widely varying proportions to give new perfume compositions, generally containing between 1 and 50% by wt., relative to tile weight of the whole composition, of the derivatives proposed.

8 Claims, No Drawings

ISOMERIC 11-OXATRICYCLO[7.3.02,6]DODECENE DERIVATIVES, THEIR PRODUCTION AND THEIR USE AS FRAGRANCES AND FRAGRANCE COMPOSITIONS CONTAINING THEM

This application is a continuation, of application Ser. No. 08/030,233 filed on Mar. 17, 1993 now abandoned.

BACKGROUND OF THE INVENTION

1. Field of the Invention

This invention relates to isomeric 11-oxatricyclo[7.3.0.0$^{2,6}$]dodecene derivatives, to a process for their production and to their use as fragrances.

2. Statement of Related Art

Some 11-oxatricyclo[7.3.0.0$^{2,6}$]dodecene derivatives are known from the literature. K. Bruns, U. Weber and M. Meiertoberens obtained Diels-Alder adducts by reaction of an isomer mixture of 2,2,4(2,4,4)-trimethyl-1-vinylcyclopent-1-ene with maleic or citraconic anhydride and itaconic and acetylene dicarboxylic acid dimethyl ester. After reduction and cyclization, the Diels-Alder adducts were converted into tricyclic ethers with a variety of woody odor notes (Parfümerie u. Kosmetik, 1986 (67) 714).

Although the ethers synthesized by Bruns et al. have good fragrance properties, there is still a need for compounds having characteristic odor profiles of different quality. Accordingly, a search was made for compounds which were to have characteristic new odor profiles coupled with good persistence, odor intensity and emanative power.

According to the invention, this problem has been solved by new 11-oxatricyclo[7.3.0.0$^{2,6}$]dodecene derivatives obtained by:

a) reaction of isomerically pure trimethylvinyl cyclopentenes (i.e. either 2,2,4- or 2,4,4-trimethyl-1-vinylcyclopent-1-ene) with maleic acid, its anhydride or dialkyl ester or by b) reaction of isomerically pure trimethylvinyl cyclopentenes (i.e. either 2,2,4- or 2,4,4-trimethyl-1-vinylcyclopent-1-ene) or mixtures of these trimethylvinyl cyclopentenes with fumaric acid or its dialkyl esters to form the corresponding Diels-Alder adducts, reduction of these adducts to the corresponding diols and subsequent cyclization.

DESCRIPTION OF THE INVENTION

Accordingly, the present invention relates to isomeric 11-oxatricyclo[7.3.0.0$^{2,6}$]dodecene derivatives corresponding to general formula I-V.

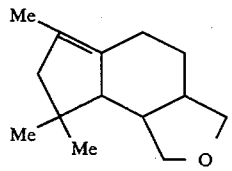
(I)

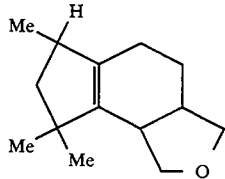
(II)

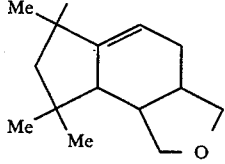
(III)

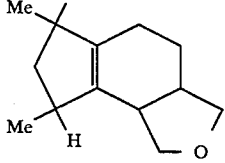
(IV)

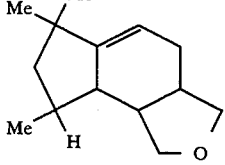
(V)

wherein the tetrahydrofuran ring is in the cis configuration and to 11-oxatricyclo[7.3.0.0$^{2,6}$]dodecene derivatives of the formula I-V a mixture thereof wherein the tetrahydrofuran ring is in the trans configuration.

The present invention also relates to the production of the isomeric 11-oxatricyclo[7.3.0.0$^{2,6}$]dodecene derivatives corresponding to general formula I-V

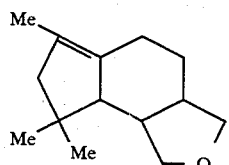
(I)

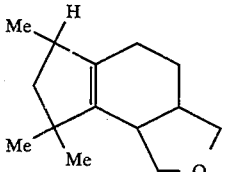
(II)

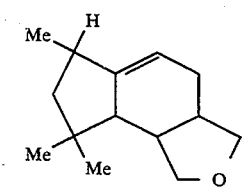
(III)

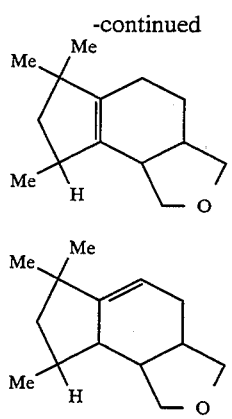

(IV)

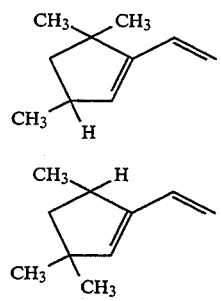

(V)

wherein the tetrahydrofuran ring is in the cis and/or trans configuration by reaction of a diene having the formula VI or VII (VI)

(VII)

with maleic acid, maleic anhydride or a maleic acid dialkyl ester or with fumaric acid or a fumaric acid dialkyl ester to form the Diels-Alder adduct, reduction of the Diels-Alder adduct to the diol and dehydrating cyclization of the diol to form the 11-oxatricyclo[7.3.0.0$^{2,6}$]dodecene derivative.

The new compounds are prepared by syntheses known per se from organic chemistry. The starting material for the 11-oxatricyclo[7.3.0.0$^{2,6}$]dodecene derivatives prepared by way of the fumaric acid adducts is, for example, an isomer mixture of 2,2,4(2,4,4)-trimethyl-1-vinylcyclopent-1-ene as described in DE-OS 29 25 622 and in the above-cited work of Bruns et al. However, it is preferred to use the isomerically pure trimethyl-1-vinylcyclopent-1-enes which may be obtained by distillation from the isomer mixture. By contrast, the isomerically pure trimethyl-1-vinylcyclopent-1-enes only are used as starting material for the 11-oxatricyclo[7.3.0.0$^{2,6}$]dodecene derivatives prepared by way of the maleic acid adducts.

The Diels-Alder adducts obtained at the beginning of the synthesis sequence are converted into the corresponding diols by chemical reduction. The reducing agent used may be, for example, sodium-bis-(2-methoxyethoxy)-aluminium dihydride, $NaAlH_2(OCH_2CH_2OCH_3)_2$, which is commercially obtainable under the name Vitride® (Paesel GmbH & Co., Frankfurt a.m.). Finally, the dehydrating cyclization of the diols, for example with p-toluenesulfonic acid or potassium hydrogen phosphate, leads to the ethers I according to the invention which, for defined stereoisomerism, are obtained as complex regioisomer mixtures.

The compounds according to the invention are fragrances having differently nuanced intensive woody odor notes and extraordinary persistence. They are distinguished from the tricyclic ethers described in the prior art by characteristic odor profiles of distinctly different quality. In addition, the compounds according to the invention prepared by way of the fumaric acid adducts are of considerably greater odor intensity and emanative power. The after-odor (evaluation after 24 hours) of the ethers according to the invention prepared by way of the fumaric acid adducts is very intensive and is dependent upon the position of the methyl substituents. The compound of Example 1 has by far the most intensive after-odor (cf. Example 1).

Accordingly, the present invention also relates to the use of the isomeric 11-oxatricyclo[7.3.0.0$_{2,6}$]dodecene derivatives as fragrances.

The compounds according to the invention may advantageously be used as structural elements for new fragrance compositions. Fragrance compositions contain, for example, natural, synthetic or partly synthetic fragrances, essential oils and plant extracts. The percentages in which the compounds according to the invention or mixtures thereof may be used in fragrance compositions are between 1 and 50% by weight, based on the mixture as a whole.

Compositions of this type may be used both for perfuming cosmetic preparations, such as creams, lotions, toilet waters, aerosols and toilet soaps, and in alcohol-based perfumery. They may also be used for perfuming industrial products, such as detergents, fabric softeners and textile treatment preparations. For perfuming these various products, the compositions are added to them in concentrations of 0.05 to 2% by weight, based on the product as a whole.

The following Examples are intended to illustrate the invention without limiting it in any way.

EXAMPLES

1. Preparation of the intermediate stages

The compounds of general formula I were prepared in a three-step synthesis starting from diene II. Diene II was present in the form of a mixture of 2,2,4-trimethyl-1-vinylcyclopent-1-ene and 2,4,4-trimethyl-1-vinylcyclopent-1-ene which had been prepared from a 50:50 mixture of 2,2,4- and 2,4,4-trimethylcyclopentan-1-one in accordance with the literature (see above). It follows from this that both the Diels-Alder adducts prepared therefrom (hereinafter designated III) and the diols obtainable therefrom (hereinafter designated IV) were present as isomer mixtures. To make the position isomerism of the three methyl groups in question clear in the nomenclature of the corresponding compounds, the position of the three methyl groups of one isomer is followed in brackets by the position of the methyl groups of the other isomer.

1.1 preparation of the Dies-Alder adducts III
1.1.1 General procedure

Diene II and dienophile in a molar ratio of 1:0.75 to 1:1.2 were heated with stirring under nitrogen for 2 to 18 hours to a temperature of 80° C. to 125° C. either directly or in a solvent. After cooling, the unreacted educt and the solvent were distilled off in vacuo and the remaining crude product was distilled, optionally in a fine vacuum. Alternatively, the crude product solution was directly introduced into the reduction step.

Compounds IIIa and IIIb described in the following were prepared by this general procedure.

1.1.2 Individual syntheses

IIIa: (1α,9α)-11-oxa-3,3,5(3,5,5)-trimethyltricyclo[7.3.0.0²,⁶]dodec-6-ene-10,12-dione 112.2 g (0.83 mol) diene II in 110 ml toluene were added dropwise over a period of 1 hour at 100° C. to 73.5 g (0.75 mol) maleic anhydride in 75 ml toluene, followed by stirring under reflux for 3 hours. The crude product solution was introduced into the reduction step without any further working up. Analytical data (crude product after removal of the solvent):

IR (film): 1855, 1780 cm$^{-1}$ ($V_{C=O}$ anhydride) $^1$H-NMR (CDCl$_3$): 5.3–5.7 ppm (m, 1H, olefin. proton) MW (GC/MS): C$_{14}$H$_{18}$O$_3$ calc.: 234.20, found: 234 (isomers)

IIIb: (2α,3β)-7,7,9(7,9,9)-trimethylbicyclo[4.3.0]non-5-ene-2,3-dicarboxylic acid di-n-butyl ester 122.4 g (0.9 mol) diene II were added dropwise over a period of 1 hour at 120° C. to 171 g (0.75 mol) fumaric acid di-n-butyl ester, followed by stirring for another 6 hours at 120° C. The crude product was introduced into the reduction step without any further working up. Analytical data:

(IR (film): 1735 cm$^{-1}$ ($V_{C=O}$ ester) MG (GC/MS): C$_{22}$H$_{36}$O$_4$ calc.: 364.53, found: 364 (isomers)

1.2 Preparation of diols IV
1.2.1 General procedure

An approx. 35% Vitride® solution in toluene was added over a period of about 1 hour in a nitrogen atmosphere to the Diels-Alder adducts III dissolved in toluene. Alternatively, the adducts III were added dropwise to a 70% Vitride® solution. The reactions took place exothermically at 45° C. to 60° C. The mixtures were then stirred under reflux for another 2 to 4 hours.

Working up:

5 ml acetone were added to the cooled reaction solution, after which approx. 180 to 210 ml distilled water were added until the aluminate precipitate flocculated. The toluene solution remaining behind was washed with 3N hydrochloric acid, saturated NaHCO$_3$ and saturated NaCl solution, dried over sodium sulfate and the toluene was removed in vacuo.

Compounds IVa and IVb described in the following were prepared by this general procedure.

1.2.2 Individual syntheses

IVa:(2α, 3α)-2,3-di-(hydroxymethyl)-7,7,9(7,9,9)-trimethylbicyclo[4.3.0]non-5-ene A solution of 470 ml (1.68 mol) Vitride® (70% in toluene) in 500 ml toluene was added over a period of 1 hour to the crude product solution IIIa, followed by stirring under reflux for 2 hours. Working up as described above. Crude product: 138.9 g. Analytical data:

IR (film): 3310, 1030 cm$^{-1}$ ($V_{O-H}$, $V_{C-O}$ alcohol) $^1$H-NMR (CDCl$_3$): 3.2–3.8 ppm (m, 6H, —CH—OH) 5.1–5.35 ppm (m, 1H, olefin. proton) MG (GC/MS): C$_{14}$H$_{24}$O$_2$ calc.: 224.35, found: 224 (isomers)

IVb:(2α,3β)-2,3-di-(hydroxymethyl)-7,7,9(7,9,9)-trimethylbicyclo[4.3.0]non-5-ene A solution of 470 ml (1.68 mol) Vitride® (70% in toluene) in 500 ml toluene was added over a period of 1 hour to crude product IIIb dissolved in 500 ml toluene, followed by stirring under reflux for 2 hours. Working up as described above. Crude product: 137.5 g. Analytical data:

IR (film): 3330, 1040 cm$^{-1}$ ($V_{O-H}$, $V_{C-O}$ alcohol) MW (GC/MS): C$_{14}$H$_{24}$O$_2$ calc.: 224.35, found: 224 (isomers)

Products IVa and IVb could be used in the following cyclization step without any further working up.

2. Preparation of compounds I according to the invention

The ethers I according to the invention were prepared from the diols IV by dehydrating cyclization.

2.1 General procedure

The crude diol IV heated to 55° C. was added dropwise to approx. 0.14 mol equivalent KHSO$_4$ at a bath temperature of 180° C. and under a pressure of 1 mbar. The cyclization product I formed was simultaneously distilled off overhead, a vapor temperature of 95° C. to 105° C. being spontaneously established. After the addition, distillation was continued for another 1.5 hours at 190° C./1 mbar and the crude product was subsequently fractionated in a fine vacuum.

The compounds of Comparison Example 1 and Examples 1 to 5 described in the following were prepared by this general procedure. At the same time, the C=C double bond was partly isomerized under the cyclization conditions. This is also apparent from the respective designations of compounds Ia and Ib.

2.2 Individual syntheses

Comparison Example 1

Preparation of an isomer mixture (Ia) consisting of: (1α,9α)-11-oxa-3,3,5(3,5,5)-trimethyltricyclo[7.3.0.0²,⁶]dodec-6-ene (A), (1α,9α)-11-oxa-3,3,5(3,5,5)-trimethyltricyclo[7.3.0.0²,⁶]²,⁶dodecene (B) and (1α,9α)-11-oxa-3,3,5-trimethyltricyclo[7.3.0.0²,⁶]dodec-5-ene (C)

Reaction: 138.9 g (approx. 0.62 mol) IVa, 12 g (0.088 mol) KHSO$_4$, dropwise addition time 5 hours. Bp$_{0.25}$: 62°C.–70° C. Yield: 92.6 g=60% of the theoretical, based on maleic anhydride Composition A:B:C=1:3:3 Odor: woody, earthy, camphory, cedar, dynamon, birch tar note Analytical data: IR (film): 1080, 912 cm$^{-1}$ ($V_{C-O-C(as)}$,ring cycl. ether) $^1$H-NMR (CDCl$_3$): 1.67 ppm ("s", 3H, —C=C—CH$_3$) 3.0–4.0 ppm (m, 4H, —CH$_2$—O—CH$_2$) 5.3–5.45 ppm (m, 1H, olefin. proton) MW (GC/MS): C$_{14}$H$_{22}$O calc.: 206.33, found: 206 (isomers)

Example 1

Preparation of an isomer mixture (Ib) consisting of: (1α,9β)-11-oxa-3,3,5(3,5,5)-trimethyltricyclo[7.3.0.0²,⁶]dodec-6-ene (A) and (1α,9β)-11-oxa-3,3,5 (3,5,5)-trimethyltricyclo[7.3.0.0²,⁶]²,⁶dodecene (B)

Reaction: 137.5 g (approx. 0.61 mol) IVb, 12 g (0.088 mol) KHSO$_4$,dropwise addition time: 5 hours Bp$_{0.3}$: 75°C.–78° C. Yield: 62.7 g=40% of the theoretical, based on fumaric acid di-n-butyl ester Composition A:B=2:1 Analytical data: IR (film): 1020, 900 cm$^{-1}$($V_{C-O-Cas}$, ring cycl. ether) $^1$H-NMR (CDCl$_3$): 3.2–4.2 ppm (m, 4H, —CH$_2$—O—CH$_2$) 5.3–5.4 ppm (m, 1H, olefin. proton) MW (GC/MS): C$_{14}$H$_{22}$O calc.: 206.33, found: 206 (isomers) Odor: woody, narcotic, strong ionone, boisambrene note; twice as strong as the corresponding cis-compound of Comparison Example 1.

The isomerically pure compounds IVa and IVb were obtained by using isomerically pure 2,2,4-trimethyl-1-vinylcyclopent-1-ene or 2,4,4-trimethyl-1-vinylcyclopent-1-ene at the beginning of the synthesis sequence II→III→IV. These compounds were also cyclized by the general procedure described above (Examples 2 to 5).

Example 2

Preparation of an isomer mixture (Ia) consisting of: (1α,9α)-11-oxa-3,5,5-trimethyltricyclo [7.3.0.0²,⁶]dodec-6-ene (A) and (1α,9α)-11-oxa-3,5,5-trimethyltricyclo[7.3.0.0²,⁶]²,⁶dodecene (B)

Composition A:B=1:2 Odor: woody, earthy, dynamon, cedar note Analytical data: IR (film): as Comparison Example 1 ¹H-NMR (CDCl₃): 3.2–4.0 ppm (m, 4H, —CH₂—O—CH₂—) 5.3–5.45 ppm (m, 1H, olefin. proton) MW (GC/MS): as Comparison Example 1

Example 3

Preparation of an isomer mixture (Ib) consisting of: (1α,9β)-11-oxa-3,5,5-trimethyltricyclo [7.3.0.0²,⁶]dodec-6-ene (A) and (1α,9β)-11-oxa-3,5,5-trimethyltricyclo[7.3.0.0²,⁶]²,⁶dodecene (B)

Composition A:B=1:1.5 Odor: woody, narcotic, strong ionone, boisambrene note, slightly fruity; very similar to Example 1, but even greater emanative power Analytical data: IR (film): as Comparison Example 1 ¹H-NMR (CDCl₃): 3.2–4.2 ppm (m, 4H, —CH₂—O—CH₂—) 5.3–5.4 ppm (m, 1H, olefin. proton) MW (GC/MS): as Comparison Example 1

Example 4

Preparation of an isomer mixture (Ia) consisting of: (1α,9α)-11-oxa-3,3,5-trimethyltricyclo[7.3.0.0²,⁶]dodec-6-ene (A), (1α,9α)-11-oxa-3,3,5-trimethyltricyclo[7.3.0.0²,⁶]²,⁶dodecene (B) and (1α,9α)-11-oxa-3,3,5-trimethyltricyclo[7.3.0.0²,⁶]dodec-5-ene (C)

Composition A:B:C=1:4:7 Odor: fruity, woody, narcotic, camphory, distinctly stronger than in Example 2 Analytical data: IR (film): 1080, 912 cm⁻¹ (ν$_{C-O-C}$ (as), ring cycl. ether) ¹H-NMR (CDCl₃): 1.68 ppm ("s", 3H, —C=C—CH₃) 3.0–4.1 ppm (m, 4H, —CH₂—O—CH₂) 5.4 ppm (m, 1H, olefin. proton) MW (GC/MS): C₁₄H₂₂O calc.: 206.33, found: 206 (isomers)

Example 5

Preparation of an isomer mixture consisting of: (1α,9β)-11-oxa-3,3,5-trimethyltricyclo[7.3.0.0²,⁶]dodec-6-ene (A) and (1α,9β)-11-oxa-3,3,5-trimethyltricyclo[7.3.0.0²,⁶]²,⁶dodecene (B)

Composition A:B = 1:1 Odor: tar, ships plank, burnt wood note, technical IR (film): as Example 1 ¹H-NMR (CDCl₃): 3.2–4.1 ppm (m, 4H, —CH₂—O—CH₂—) 5.3–5.45 ppm (m, 1H, olefin. proton) MW (GC/MS): as Example 1

Composition Example

| "Polo" type men's note | Parts by weight |
|---|---|
| Citrus oil 67 | 200 |
| Lavendar oil, real | 30 |
| Eucalyptus oil Globulus | 40 |
| Juniper berry oil | 10 |
| Nutmeg oil | 25 |
| Aldehyde C-12 (MNA) | 2 |
| Phenyl acetaldehyde dimethyl acetal | 3 |
| Methyl dihydrojasmonate | 170 |
| Jasmonan (Henkel) | 10 |
| o-Tert.butyl cyclohexyl acetate | 3 |
| Cyclovertal (Henkel) | 2 |
| Coumarin | 25 |
| Lyral | 60 |
| α-n-Methyl ionone | 20 |
| Iso-E-Super (IFF) | 100 |
| Kephalis (Roure Bertrand) | 30 |
| Clary oil | 20 |

-continued

| "Polo" type men's note | Parts by weight |
|---|---|
| Cassis synth. (Firmenich) | 10 |
| Ambroxan 10% (Henkel) | 15 |
| Eugenol | 15 |
| Musk ketone | 30 |
| Galaxolide 50 (IFF) | 70 |
| Cyclohexyl salicylate (Henkel) | 10 |
| Evernyl (Roure Bertrand) | 20 |
| Ib-1 (Example 1) or Ia-1 (Example 4) | 70 |
| | 1000 |

What is claimed is:

1. A compound selected from the group consisting of a compound of the formula I, II, III, IV, V, and a mixture thereof

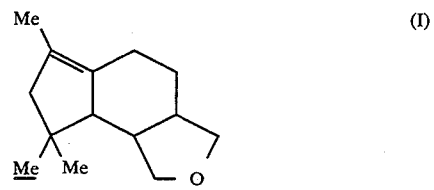

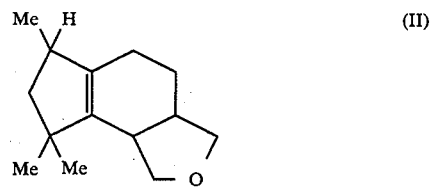

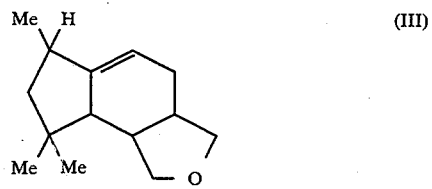

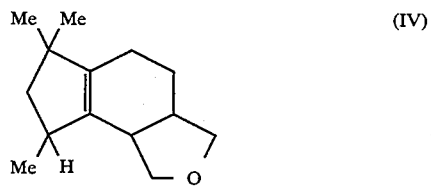

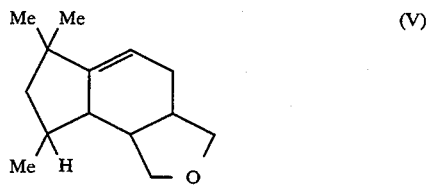

wherein the tetrahydrofuran ring is in the trans configuration.

2. A fragrance composition comprising from about 1% to about 50% by weight of a compound of claim 1.

3. An isomer mixture consisting essentially of (1α,9β)-11-oxa-3,3,5(3,5,5)-trimethyltricyclo(7.3.0.0²,⁶)dodec-6-ene and (1α,9β)-11-oxa-3,3,5(3,5,5)-trimethyltricyclo(7.3.0.0²,⁶)²,⁶dodecene.

4. An isomer mixture consisting essentially of (1α,9β)-11-oxa-3,5,5-trimethyltricyclo(7.3.0.0²,⁶)dodec-6-ene and (1α,9β)-11-oxa-3,5,5-trimethyltricyclo(7.3.0.0²,⁶)²,⁶dodecene.

5. An isomer mixture consisting essentially of (1α,9β)-11-oxa-3,3,5-trimethyltricyclo(7.3.0.0$^{2,6}$)dodec-6-ene and (1α,9β)-11-oxa-3,3,5-trimethyltricyclo(7.3.0.0$^{2,6}$)$^{2,6}$dodecene.

6. A fragrance composition comprising from about 1% to about 50% by weight of the isomer mixture of claim 3.

7. A fragrance composition comprising from about 1% to about 50% by weight of the isomer mixture of claim 4.

8. A fragrance composition comprising from about 1% to about 50% by weight of the isomer mixture of claim 5.

* * * * *